United States Patent
Haverkamp et al.

(10) Patent No.: US 10,067,028 B2
(45) Date of Patent: Sep. 4, 2018

(54) CALIBRATION STRUCTURE AND CALIBRATION METHOD FOR CALIBRATING OPTICAL MEASURING DEVICES

(71) Applicant: Carl Zeiss Industrielle Messtechnik GmbH, Oberkochen (DE)

(72) Inventors: Nils Haverkamp, Aalen (DE); Dominik Seitz, Schwaebisch Gmuend (DE)

(73) Assignee: CARL ZEISS INDUSTRIELLE MESSTECHNIK GMBH, Oberkochen (DE)

( * ) Notice: Subject to any disclaimer, the term of this patent is extended or adjusted under 35 U.S.C. 154(b) by 0 days.

(21) Appl. No.: 15/706,723

(22) Filed: Sep. 17, 2017

(65) Prior Publication Data
US 2018/0088001 A1    Mar. 29, 2018

(30) Foreign Application Priority Data
Sep. 23, 2016    (DE) .......................... 10 2016 218 360

(51) Int. Cl.
*G01M 11/02*    (2006.01)

(52) U.S. Cl.
CPC .... *G01M 11/0285* (2013.01); *G01M 11/0207* (2013.01); *G01M 11/0264* (2013.01)

(58) Field of Classification Search
USPC .................. 382/199, 203; 348/135, 136, 140
See application file for complete search history.

(56) References Cited

U.S. PATENT DOCUMENTS

| | | | |
|---|---|---|---|
| 5,196,900 A * | 3/1993 | Pettersen | G01B 11/00 356/141.4 |
| 6,538,691 B1 | 3/2003 | Macy et al. | |
| 6,615,099 B1 * | 9/2003 | Muller | B23K 26/04 219/121.68 |

(Continued)

FOREIGN PATENT DOCUMENTS

| | | |
|---|---|---|
| DE | 19805040 A1 | 8/1999 |
| JP | H08-170907 | 7/1996 |

OTHER PUBLICATIONS

Patterned chrome datasheet, Materion Barr Precision Optics and Thin Film Coatings, URL: https://materion.com/-/media/files/pdfs/precision-optics/data-sheets-2012/patterned-chrome-data-sheet.pdf, retrieved on Sep. 20, 2017.

(Continued)

*Primary Examiner* — Ishrat I Sherali
(74) *Attorney, Agent, or Firm* — Ewers & Hasselmann PLLC (57) ABSTRACT

A calibration structure for calibrating optical measuring devices is provided. The calibration structure includes a plurality of zones adjoining one another in a plane, wherein the zones adjoin one another along straight lines and/or curved lines and the calibration structure has both zones adjoining one another along straight lines and zones adjoining one another along curved lines, wherein the zones adjoining one another along straight lines or the zones adjoining one another along curved lines have respectively mutually different optical properties. Furthermore, a calibration method for calibrating the optical measuring devices by the calibration structure is provided.

17 Claims, 4 Drawing Sheets

(56) References Cited

U.S. PATENT DOCUMENTS

| | | | |
|---|---|---|---|
| 7,457,478 B2* | 11/2008 | Aoyama | G06T 3/0018 348/E5.078 |
| 7,541,121 B2* | 6/2009 | Ziger | G03F 7/70516 430/30 |
| 8,406,562 B2* | 3/2013 | Bassi | H04N 9/3147 348/222.1 |
| 8,717,442 B2* | 5/2014 | Inui | B60R 1/00 348/175 |
| 9,019,351 B2* | 4/2015 | Yu | H04N 13/02 348/48 |
| 9,068,820 B2* | 6/2015 | Kosmecki | A61B 1/00057 |
| 9,417,184 B2* | 8/2016 | Wimmer | G01N 21/4785 |
| 2003/0137655 A1 | 7/2003 | Wegmann | |
| 2010/0225666 A1 | 9/2010 | Beauchemin | |
| 2014/0104419 A1* | 4/2014 | Metzler | G01C 15/002 348/140 |
| 2016/0131476 A1* | 5/2016 | Haverkamp | G01B 21/042 73/1.79 |
| 2016/0260218 A1* | 9/2016 | Zweig | G06T 7/80 |
| 2016/0261851 A1* | 9/2016 | Tian | G06T 7/80 |

OTHER PUBLICATIONS

Materion Coatings and Films; URL: http://materion.com/ResourceCenter/ProductData/PrecisionOptics/CoatingsandFilms.aspx, archived at http://www.archive.org on Apr. 2, 2016, retrieved on Sep. 20, 2017.

Office Action issued in German Patent Application No. DE 10 2016 218 360.5 (from which this application claims priority), dated Sep. 21, 2017 and English language machine translation thereof.

Novel Calibration and Lens Distortion Correction of 3D Reconstruction Systems; Journal of Physics: Conference Series 48 (2006); p. 359-363.

Investigation of a 3D system distortion correction method for MR images; Journal of Applied Clinical Medical Physics, vol. 11, No. 1, Winter 2010; p. 200-216.

Real-time geometric lens distortion correction using a graphics processing unit; Optical Engineering 51(2), 027002 (Feb. 2012); p. 027002-1-027002-5.

* cited by examiner

CALIBRATION STRUCTURE AND CALIBRATION METHOD FOR CALIBRATING OPTICAL MEASURING DEVICES

CROSS REFERENCE TO RELATED APPLICATIONS

This application claims priority from German patent application DE 10 2016 218 360.5, filed Sep. 23, 2016, the entire content of which is incorporated herein by reference.

TECHNICAL FIELD

The present invention relates to a calibration structure and a calibration method for calibrating optical measuring devices. In particular, the invention relates to a method for calibrating a so-called profile projector, i.e., a measuring device, which provides a 2D image of the measurement object on a display in order to measure for example the position and/or the profile of an object edge.

BACKGROUND

DE 198 05 040 A1 describes a generic measuring device having a workpiece table for supporting a measurement object and a camera that is arranged above the workpiece table and that is displaceable vertically downwardly. Arranged below the workpiece table is a light source that illuminates the measurement object in what is known as transmitted light. The image recorded with the camera consequently shows the measurement object as a silhouette. However, more specific details of the measurement method are not described therein.

One example of a digital profile projector is described in United States Patent Application Publication No. 2010/0225666 A1. This profile projector generates a digital image of a measurement object, and a drawing of the measurement object is superimposed on the image display so as to be able to check whether the measurement object corresponds to the drawing within predetermined workpiece tolerances.

The imaging object of a real optical system and consequently also the camera of a real optical measuring device are known to always exhibit imaging aberrations that can be traced back in part to manufacturing tolerances and in part to trade-offs during the optical design and/or to underlying physical phenomena. The imaging aberrations represent the deviation of the real imaging optics from an ideal optical imaging that is possible only in theory. Typical imaging aberrations include spherical aberration, astigmatism, coma, image field curvature (focal plane deviation-FPD) and distortion. For increasing the measurement accuracy of an optical measuring device, the imaging aberrations in the image recorded by the imaging optics can be corrected by way of computation before, during or after the actual image evaluation, wherein correction values obtained in a previous calibration operation are used. U.S. Pat. No. 6,538,691 B1, for example, describes a computer-implemented correction of image distortions of a digital camera.

The known methods and measuring devices and the calibration methods used therein are not yet optimal, especially in cases where the imaging optics can be adjusted at different working distances from a workpiece table. The imaging aberrations are frequently minimized in optimum fashion only for a specific working distance.

Furthermore, the known methods and measuring devices generally proceed from a point image approximation in which for example the distortion is taken into account merely as a scale error in the imaging of a point, as a result of which higher-order imaging aberrations which affect the distortion are not taken into account. Furthermore, the known methods and measuring devices also do not take into account that even the image evaluation performed by software, for example in the form of edge evaluations, has an impact on the ascertained distortion of the measuring device.

SUMMARY

It is an object of the present invention to provide a calibration structure and a calibration method of the type described in the introduction, which on the one hand make it possible to obtain accurate calibration data for an optical measuring device taking account of higher-order imaging aberrations and also taking account of the influence of the evaluation software and thereby enable on the other hand an efficient measurement with regard to measurement time and costs on a measurement object with high measuring accuracy by the calibrated optical measuring device.

In accordance with a first aspect of the invention, this object is achieved by providing a calibration structure for calibrating optical measuring devices, wherein the calibration structure includes a plurality of zones adjoining one another in a plane. The zones adjoin one another along straight lines and/or curved lines and the calibration structure has zones adjoining one another along straight lines and zones adjoining one another along curved lines. The zones adjoining one another along straight lines or the zones adjoining one another along curved lines have respectively mutually different optical properties.

The calibration structure according to an aspect of the invention differs from conventional calibration structures having checkered patterns by additional curved lines which separate in a manner corresponding to the known checkered patterns mutually adjoining zones of different optical properties. The additional curved lines make it possible to accommodate a higher density of zones having different optical properties per unit area on the calibration structure and at the same time to increase the length of all lines meeting at a crossing point for obtaining calibration values. In this case, it should be taken into consideration that curved lines in the form of circle arcs can be evaluated just as easily as straight lines with regard to an edge evaluation. Corresponding software algorithms are available in standard libraries for image evaluation or image processing.

The novel calibration structure according to an aspect of the invention makes it possible, within the object field to be considered of an optical measuring device, to evaluate the distortion at more support points of the object field than hitherto. This applies in particular to optical measuring devices in which conventional calibration structures having the known checkered pattern have already reached the lateral resolution limit of the optical measuring device in the object field with the period length of the checkered pattern. A further densification of the checkered pattern to increase the support point density for a distortion calibration is pointless in such a case.

Accordingly, in comparison with a known calibration structure having a checkered pattern, given the same period length of the pattern, the novel calibration structure according to an aspect of the invention allows a significant increase in the number of support points for a distortion correction or distortion calibration. As a result, even higher-order imaging aberrations which influence the distortion of the image field and which are distinguished by a higher lateral spatial frequency or lower period length in the image field can be registered by the calibration. Furthermore, the novel calibration structure according to an aspect of the invention makes it possible to better determine the influence of the evaluation software on the ascertained distortion since, on the one hand, the support point density is increased and since, on the other hand, the number of changes of the optical properties at the straight and at the curved lines is also increased. As a result, it is possible to find in a closely neighboring fashion not only points having a transition of the optical property from, for example, bright to dark, but also points having the opposite transition from dark to bright, such that a possible image aberration on account of an inadequate edge evaluation by software, which image aberration, e.g., shifts the edge position of the bright-dark transition more into the dark zones, can be corrected by a corresponding evaluation of the neighboring points having the opposite transition.

In one exemplary embodiment, the respectively mutually different optical properties are given by the complementary optical properties of the respective other zone. In the context of the present invention, a complementary optical property is understood to mean an opposite optical property of the respective zones of the calibration structure such as bright to dark, reflecting to absorbing, left circularly to right circularly polarizing, or else a complementary color such as red to cyan, green to magenta or blue to yellow, etc. However, these complementary optical properties of the respective zones of the novel calibration structure according to an aspect of the invention may also occur only under specific illumination situations, such as a transmitted-light illumination or reflected-light illumination, for example. Correspondingly, different illumination wavelengths can also lead to complementary optical properties. Likewise, the polarization state of the illumination light in interaction with the respective zones can lead to a complementary optical property of the respective zones. Complementary optical properties have the advantage, that they can be utilized with regard to the edge evaluation by software to the effect that, in the case of the calibration structure according to an aspect of the invention, the transition from zones having complementary optical properties takes place adjacently to a different transition of zones having opposite properties, such that, from the consideration of the differences between the neighboring transitions, conclusions can be drawn about inadequacies of the evaluation of the transition by software and the actual aberrations of the imaging optics can thus be separated from those of the evaluation software.

In a further exemplary embodiment, the optical properties in this case include at least one of the following properties: transmissivity, reflectivity and polarization capability. Calibration structures having the optical properties can be produced cost effectively, for example by vapor deposition on glass plates. Furthermore, corresponding calibration structures can be used both by reflected-light illumination and by transmitted-light illumination. With the use of a corresponding chromium layer mask as a calibration structure, the latter has the advantage that the optical properties of the zones transform their respective optical properties into the optical properties complementary thereto upon the switchover from reflected-light illumination to transmitted-light illumination. Consequently, by determining the differences between the recordings of the calibration structure with varying illumination, the error in respect of edge evaluation by software can be directly determined for each of the pixels, without this necessitating a consideration of the pixels in the neighborhood.

In one exemplary embodiment, the calibration structure includes a plate-shaped substrate material, and the optical properties of some of the zones result from a coating of the plate-shaped substrate material. As a result, particularly cost-effective calibration structures can be produced, since for example the covering of plate-shaped substrate materials during the coating process can be realized in a simple manner.

In a further exemplary embodiment, the plate-shaped substrate material is a plate-shaped glass carrier and the coating is realized by a chromium coating. Such a calibration structure can be produced cost effectively by lithographic methods and offers the reversal of the optical properties of the zones upon the switchover from reflected-light to transmitted-light illumination of an optical measuring device.

In another exemplary embodiment, the plate-shaped substrate material is a plate-shaped glass carrier and the coating realizes a bandpass filter which transmits more illumination light having a wavelength of less than 500 nm with a normal incidence angle than illumination light having a wavelength of more than 600 nm, or vice versa. This exemplary embodiment is an alternative embodiment to the chromium coating which, just like the latter, brings about a reversal of the optical properties of the zones upon the switchover from reflected-light to transmitted-light illumination of an optical measuring device.

In a further exemplary embodiment, the plate-shaped substrate material is a plate-shaped glass carrier and the coating realizes a so-called polarization filter. For this purpose, in general, thin metal layers having a fine strip structure are deposited on the glass carrier. The wire grid polarizers thus produced allow only the electromagnetic waves that are linearly polarized transversely with respect to the strip structure to pass through the polarizer. Particularly in conjunction with a light-emitting diode (LED) or a liquid-crystal display (LCD) light source for transmitted-light illumination, which itself in turn generally generates linearly polarized illumination light, it is thus possible to generate the effect of the calibration structure according to an aspect of the invention during use of the transmitted-light illumination by virtue of the fact that in this case the zones with the corresponding coating block the polarized illumination light during passage.

In one exemplary embodiment, the respectively mutually different optical properties are given only for a specific wavelength in the range of between 400 nm and 700 nm and the respectively mutually different optical properties have other optical properties at a different wavelength of the range, such that the ratio of the optical properties at the different wavelength is reversed in comparison with the ratio of the optical properties at the specific wavelength. This likewise has the advantage that through the choice of the illumination wavelength for the illumination of the calibration structure, it is possible to switch over between the complementary optical properties of the zones of the calibration structure, such that by considering the differences between the recordings of the calibration structure with varying illumination wavelengths, the error in edge evaluation by software can be directly determined for each of the pixels, without this necessitating a consideration of the pixels in the neighborhood.

In one exemplary embodiment, the calibration structure has points at which a plurality of zones meet and which are distinguished as intersection points of the straight and the curved lines, wherein the calibration structure has at least one region with a regular sequence of the zones and lines, which results in a regular arrangement of the points, which regular arrangement is given by a regular shortest distance with the length L of the points with respect to one another, wherein the straight lines and the curved lines in the form of circle arcs begin at a point and end at a neighboring point relative thereto, and wherein the length of all lines beginning or ending at a point is more than 4*L, in particular more than 9*L. By virtue of the fact that the curved lines and the straight lines in this exemplary embodiment of the calibration structure according to the invention begin or end at intersection points of the calibration structure, the zones all-around the intersection points constitute something similar to a target star for determining the resolution capability of the optical measuring device. As a result, it is possible, as an alternative or in addition to the above-discussed possibilities of the consideration of differences between complementary optical properties, which become reversed, of neighboring points of the calibration structure or the consideration of differences in the edge evaluation in the case of different illumination situations, to perform an assessment of the influence of software inadequacies during the edge evaluation on the distortion measurement.

As a result of the target-star-like surface structure of the calibration structure according to an aspect of the invention, on the basis of known contrast evaluations it is possible to ascertain which points of a transition of zones of the calibration structure are still imaged with a sufficient resolution capability by the optical measuring device, and which are not. Consequently, those points for which the resolution capability is insufficient can be excluded from a further edge evaluation for the distortion calibration of the optical measuring device. Therefore, the distortion calibration is influenced only by those points of the imaged calibration structure which also exhibit a sufficient contrast and thus are also beset by a low software inadequacy with regard to the edge evaluation of a zone transition.

In a further exemplary embodiment of the invention, the calibration structure has at least one further region with at least one further zone, wherein the at least one further region or the at least one further zone has no or a sequence of zones and/or lines that is different from the at least one region with a regular sequence of zones and lines. By virtue of the fact that at least one region of the calibration structure deviates from the remaining regions of the calibration structure in terms of its symmetry-determining zones and/or lines, it is possible to separate the calibration error on account of intrinsic errors of the calibration structure from the calibration error on account of the imaging aberrations of the optical measuring device by virtue of the region in question with deviating symmetry being positioned for calibration purposes at different field points of the measurement field.

In accordance with a second aspect of the invention, the object is achieved by providing a method for calibrating optical measuring devices by a calibration structure according to an aspect of the invention, wherein the method including the steps of:
  positioning the calibration structure within the measurement range of the optical measuring device;
  illuminating the calibration structure by a reflected-light illumination and/or transmitted-light illumination;
  recording of the calibration structure by a sensor chip of the optical measuring device;
  evaluating the recording made regarding the edge positions of the calibration structure within the recording;
  calculating correction values based on the ascertained edge position;
  storing the correction values in a correction file.

By virtue of the fact that by the method according to an aspect of the invention, based on the calibration structure according to an aspect of the invention, the edge positions of transitions of the optical properties of the different zones are determined in the recordings or images made, it is possible to obtain calibration values for the optical measuring device which correspond to the offset of the recorded edges relative to nominal setpoint positions of the edges in an ideal optical measuring device. Consequently, future recordings of the optical measuring device can be corrected taking account of these calibration values stored in a correction file. According to an aspect of the invention, the use of the novel calibration structure according to an aspect of the invention for the calibration method has the effect of achieving a higher density of calibration values per area content of the recording or image made in comparison with conventional calibration structures having checkered patterns. As a result, firstly the influence of higher-order imaging aberrations and secondly the influence of the software evaluation of edge positions on the distortion error ascertained are taken into account to a greater extent than hitherto.

In an exemplary embodiment of the method according to an aspect of the invention, the steps of illuminating a calibration structure; making a recording; evaluating the recording and calculating correction values are carried out for two different illumination situations and/or two different illumination wavelengths and calculating correction values is carried out based on a consideration of the difference between the two recordings of the calibration structure that are made. As already mentioned above, it is possible, based on a consideration of the differences in the edge valuation in the case of different illumination situations or different illumination wavelengths, to perform an assessment of the influence of software inadequacies during the edge evaluation on the distortion measurement.

In one configuration, in this case one of the two illumination situations are given by a reflected-light illumination and the other of the two illumination situations is given by a transmitted-light illumination. The consideration of differences can thereby be performed for example based on a cost-effective chromium mask as calibration structure according to an aspect of the invention.

In a further configuration, for one of the two illumination situations a specific degree of polarization of the illumination light is set which differs from the degree of polarization of the illumination light of the other of the two illumination situations. This configuration of the method according to an aspect of the invention in association with a correspondingly configured calibration structure according to an aspect of the invention represents a simple possibility of generating complementary optical properties of the different zones for example in the case of monochromatic reflected-light or transmitted-light illumination.

In a further configuration, one of the two illumination wavelengths for recording the calibration structure is less than 500 nm, and the other of the two different illumination wavelengths for recording the calibration structure is more than 600 nm. It is thereby possible, in turn, particularly in association with reflected-light illumination and a calibration structure which is colored according to an aspect of the invention, to generate complementary optical properties of the different zones in a simple manner.

BRIEF DESCRIPTION OF THE DRAWINGS

The invention will now be described with reference to the drawings wherein.

DESCRIPTION OF EXEMPLARY EMBODIMENTS

Figure 1:
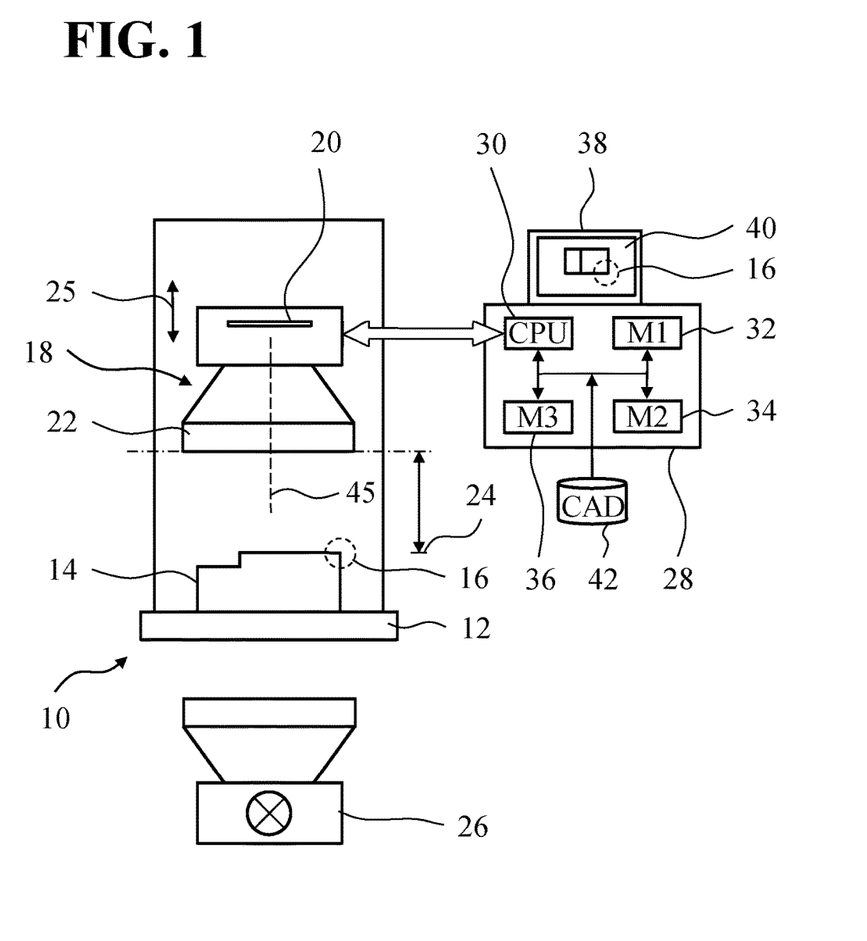
FIG. 1 shows a schematic illustration of an optical measuring device.

FIG. 1 shows an exemplary embodiment of the measuring device 10. The measuring device 10 has a workpiece table 12, on which a measurement object 14 is arranged. The reference numeral 16 designates a region of interest (ROI), in which for example an edge of the measurement object 14 extends. The intention is, for example, to measure the position of the edge and/or the edge profile.

Arranged above the workpiece table 12 is a camera 18 having an image sensor 20 and an imaging optical unit 22. The camera 18 thus views the measurement object 14 perpendicularly from above, which is a typical arrangement for such measuring devices. Alternatively, or additionally, the camera 18 or a further camera (not illustrated here) could, however, be arranged in a different orientation relative to the measurement object.

The image sensor 20 in the exemplary embodiments is a complementary metal-oxide-semiconductor (CMOS) or charge-coupled device (CCD) sensor having a plurality of pixels that are arranged in a matrix. The imaging optical unit 22 in exemplary embodiments is an imaging optical unit that is telecentric at least on the object side. In some exemplary embodiments, the imaging optical unit 22 is telecentric on the object side and on the image side. In principle, however, the imaging optical unit 22 could also be a non-telecentric imaging optical unit. In each case, the imaging optical unit 22 includes optical elements (not illustrated here), in particular lenses with which the measurement object 14 is imaged in a manner known per se onto the image sensor 20. In reality, the imaging is not ideal, i.e., the imaging optical unit 22 has imaging aberrations that are due to its construction and/or individual imaging aberrations, with the result that the image of the measurement object 14 recorded by the image sensor 20 deviates from the real measurement object 14. In particular, the imaging optical unit 22 can exhibit a focus-dependent distortion. Due to the distortion, the edge in the region of interest 16 can appear to have been shifted, rotated and/or distorted in the camera image, which is disadvantageous with respect to the measurement accuracy. For increasing the measurement accuracy, it is therefore customary to correct the image that is recorded by the image sensor 20 based on calibration values by way of computation. The calibration values are typically determined at a calibration structure having known dimensional properties; in this respect, see the description of FIGS. 2 to 6 below.

As indicated by the reference numeral 24, the camera 18 has an adjustable working position, or an adjustable working distance 24 relative to the workpiece table 12 and the measurement object 14 arranged thereon. The working distance 24 correlates with the focus setting of the imaging optical unit 22 on the measurement object 14. Different focus settings therefore correspond to different working positions. In some exemplary embodiments, the camera 18 can be displaced perpendicularly to the workpiece table 12, which is indicated here by arrow 25. This adjustment direction is typically referred to as the Z axis. Alternatively, and/or additionally, the imaging optical unit can have variable focus settings, which is implemented, for example, by lens elements which are movable relative to one another. In some exemplary embodiments, the camera 18 can additionally be displaced relative to the workpiece table 12, or the measurement object 14, within a horizontal plane, typically referred to as XY plane. In other exemplary embodiments, the camera 18 and the workpiece table 12 can be arranged rigidly with respect to one another in the XY plane.

Reference numeral 26 designates an illumination unit, which in this case is arranged below the workpiece table 12. Accordingly, the workpiece table 12 is, in this exemplary embodiment, at least partially light-transmissive. The measurement object 14 is here arranged between the camera 18 and the illumination unit 26, such that the camera 18 records the workpiece 14 using what is known as transmitted-light illumination. Alternatively, or additionally, the measuring device 10 can in other exemplary embodiments have what is known as reflected-light illumination, with which the measurement object 14 is illuminated from above or at an angle with respect to the viewing direction of the camera 18.

The reference numeral 28 designates an evaluation and control unit. The evaluation and control unit 28 controls the working position of the camera 18 relative to the measurement object 14, and the image recording. In addition, the evaluation and control unit 28 permits the image evaluation and thus the determination of measurement values that represent the needed dimensional properties of the measurement object. Moreover, the evaluation and control unit 28 carries out the correction of the image recorded by the camera 18 on the basis of the calibration values.

To this end, the evaluation and control unit includes processor 30 and one or more memories 32, 34, 36, i.e., non-transitory computer readable storage media, which are connected to the processor 30 for communication therewith. Illustrated by way of example here is a first memory 32, in which the calibration values are stored that represent the individual imaging aberrations of the imaging optical unit 22 for a defined working position 24. The calibration values in the memory 32 thus permit computational correction of the imaging aberrations.

Reference numeral 38 designates a display, which represents an interface via which a user can define one or more regions of interest 16. In some exemplary embodiments, the display 38 is a touchscreen monitor, and the user can specify one or more regions of interest 16 based on a displayed image 40 of the measurement object 14. In some exemplary embodiments, the regions of interest can be defined based on CAD data 42 that represent setpoint properties of the measurement object 14. Alternatively, or additionally, the display 38 can display a current image of the measurement object 14, and the user can define regions of interest 16 based on the current image. It goes without saying that, alternatively or additionally to a touchscreen monitor, operation using a mouse and/or keyboard or another input medium is possible.

In the subsequent figures and in the corresponding descriptions of these figures, identical reference signs in each case designate the same elements as in FIG. 1. However, the calibration structures and calibration methods described below are not restricted to use in the case of the optical measuring device 10 described in FIG. 1, but rather can also be used in the case of other optical measuring devices.

Figure 2:
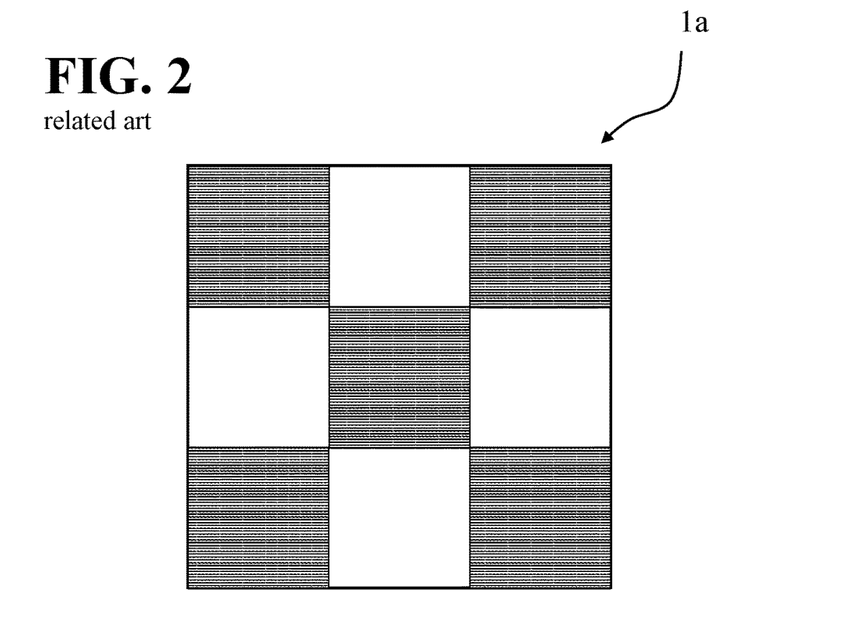
FIG. 2 shows a schematic illustration of a calibration structure from the related art with a checkered pattern.

FIG. 2 shows a schematic illustration of a calibration structure 1a from the related art with a checkered pattern for the calibration of optical measuring devices, such as, for example, the optical measuring device 10 in FIG. 1. Such calibration structures 1a from the related art are generally realized by chromium masks on glass carriers, in which the regions not covered by chromium are light-transmissive and thus appear bright in the case of a transmitted-light illumination in the camera image of the optical measuring device 10. In an alternative reflected-light illumination, by contrast, the regions covered with chromium are reflective and thus appear bright in the camera image of the optical measuring device 10.

The camera images of the optical measuring device 10 that are recorded with such a calibration structure 1a can be examined with regard to the edge position of a bright-dark transition by standard software. It is thus possible to determine the position of all the edges of the calibration structure 1a in the image of the camera 18. The position of the edges will be distorted on account of the imaging aberrations of the imaging optical unit 22, that is to say, that the edges will not extend along straight lines nor will they intersect exactly at right angles. In general, a barrel or pincushion distortion of the imaging optical unit 22 as imaging aberration will be responsible to a first approximation for this deviation of the edge position from an ideal line pattern of a checkerboard. The ideal or exact line pattern is given here by the checkered pattern of the calibration structure 1a, which can generally be produced with negligible defects in comparison with the imaging aberrations of the imaging optical unit 22.

Disregarding the production defects of the calibration structure 1a, therefore, the deviations of the ascertained edge position relative to an ideal line pattern given by mathematical equations for the straight lines of the line pattern thus represent the measurement errors of the imaging optical unit 22 of the optical measuring device 10. These deviations or measurement errors ascertained with respect to the local measurement points of the measurement field can be stored as calibration values in a file or a memory 32 of the optical measuring device 10 and can be used for the correction of future measurements. During such a correction, the locally ascertained edge position of the measurement image is then corrected by the deviation absolute value of the stored calibration values at this local position of the measurement field.

Figure 3:
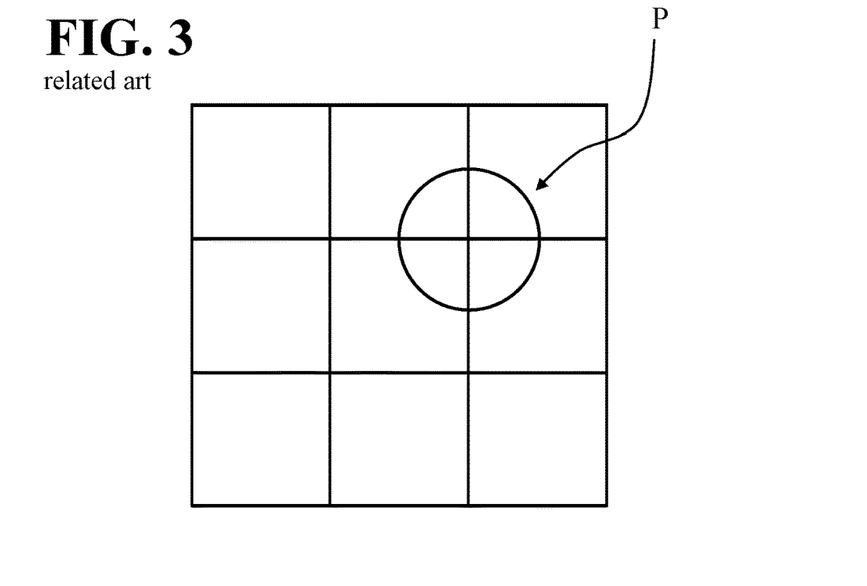
FIG. 3 shows a schematic illustration of the separating lines and intersection points of the calibration structure from the related art with a checkered pattern in accordance with FIG. 2.

FIG. 3 shows the ideal line pattern of the calibration structure 1a as a schematic illustration of the separating lines and intersection points of the calibration structure 1a with a checkered pattern in accordance with FIG. 2. The surroundings P of an intersection point of the separating lines are highlighted in FIG. 3. Two separating lines of the calibration structure 1a intersect at the intersection point. If each of the intersection points of the calibration structure 1a is then assigned a total length of the separating lines meeting at the intersection point, the total length at each of the intersection points is 2*L, wherein L is given by the edge length of one of the checkerboard fields. For elucidation, this is highlighted by the circular surroundings P of an intersection point in FIG. 3, the surroundings P enclosing two sections of two separating lines having the total length of 2*L which intersect at the intersection point.

Consequently, in the case of a calibration structure 1a from the related art, the surroundings of a field point of the measurement field of an optical measuring device 10, which can simply be equated with an intersection point for the subsequent consideration without restriction of the generality, can be calibrated based on an edge evaluation of edges of the total length of 2*L.

An increase in the calibration accuracy for an optical measuring device 10 by traditional calibration structures 1a from the related art means that the total length of the evaluatable edges of the calibration structure 1a must be increased. In association therewith, however, the number of checkerboard fields per unit area of the calibration structure 1a must be increased. This procedure of using an ever finer checkered pattern for increasing the calibration accuracy is practical, however, only until the resolution limit of the imaging optical unit 22 of an optical measuring device 10 is reached. After the resolution limit has been reached, it is no longer possible to obtain more accurate or more highly resolved calibration values for the measurement field of the optical measuring device 10.

Figure 4:
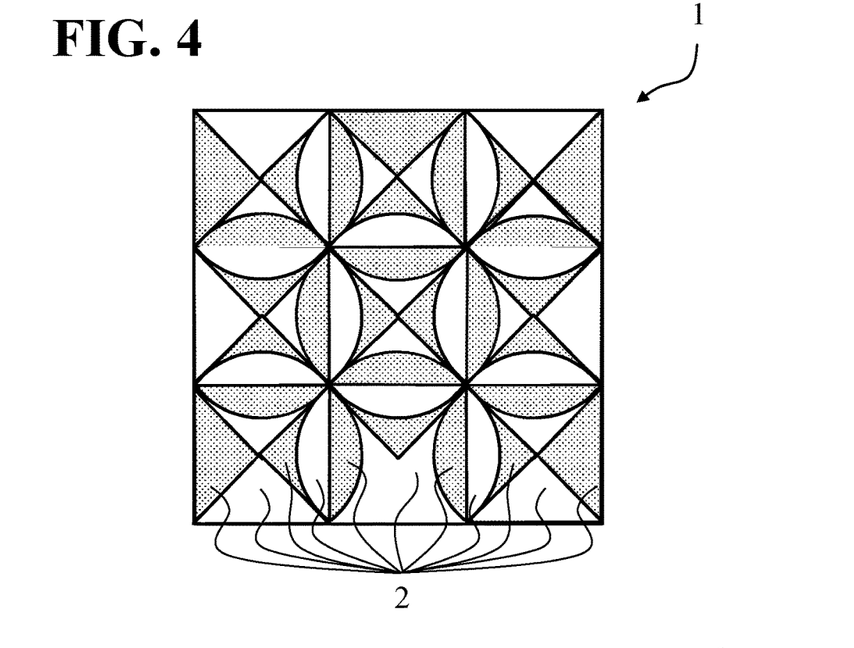
FIG. 4 shows a schematic illustration of the calibration structure according to an exemplary embodiment of the invention.
Figure 5:
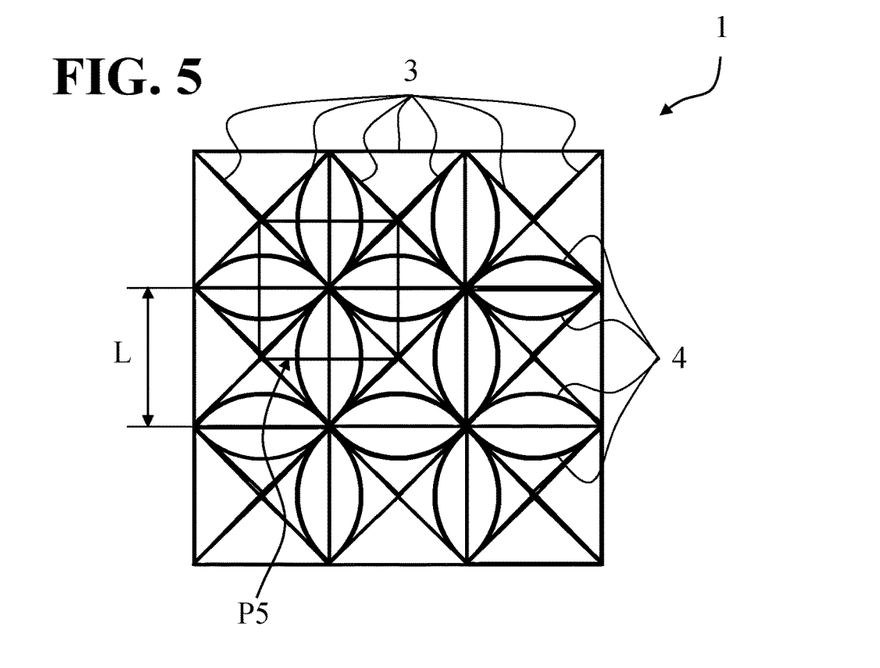
FIG. 5 shows a schematic illustration of the separating lines and intersections of the calibration structure according to the exemplary embodiment of the invention in accordance with FIG. 4.

FIG. 4 shows a schematic illustration of the calibration structure 1 according to an exemplary embodiment of the invention, wherein FIG. 5 shows, analogously to FIG. 3, a schematic illustration of the separating lines and intersection points of the calibration structure 1 according to the exemplary embodiment of the invention in accordance with FIG. 4.

The calibration structure 1 in FIG. 4 for calibrating optical measuring devices is distinguished by a plurality of zones 2 adjoining one another in a plane, wherein the zones 2 adjoin one another along straight lines 3 and/or curved lines 4. In this case, the calibration structure 1 has both zones 2 adjoining one another along straight lines 3 and zones 2 adjoining one another along curved lines 4. Those zones 2 which adjoin one another along straight lines 3, or those zones 2 which adjoin one another along curved lines 4 have respectively mutually different optical properties.

By way of example, a zone of the calibration structure 1 according to an exemplary embodiment of the invention, analogously to a zone of the calibration structure 1a in FIG. 2, can be distinguished by a chromium coating on a glass carrier, and an adjoining zone can be distinguished just by the uncoated glass carrier. These two zones have respectively mutually different optical properties. The zone with the chromium coating is light-nontransmissive during transmitted-light illumination and therefore appears dark in the camera image. By contrast, the zone with chromium coating is reflective during reflected-light illumination and therefore appears bright in the camera image. The adjoining zone with the uncoated glass carrier has different optical properties with respect thereto. The zone appears bright in the camera image during transmitted-light illumination, and dark during reflected-light illumination owing to lack of reflection.

In particular, the respectively mutually different optical properties of the adjoining zones 2 of the calibration structure 1 according to the exemplary embodiment of the invention in FIG. 4 can be given by the complementary optical properties of the respective other zone 2, as has already been mentioned initially and as is the case for example for the chromium mask mentioned above.

Alternatively, or additionally, for this purpose the calibration structure 1 can also consist of a glass carrier, on which a bandpass filter is realized in some of the zones 2 by a coating, wherein the bandpass filter transmits more illumination light having a wavelength of less than 500 nm with a normal incidence angle than illumination light having a wavelength of more than 600 nm, or vice versa. As a result, it is possible for example to shift the illumination light into the bluish spectral range upon passage in the coated zones in contrast to the uncoated zones, or vice versa, as a result of which the spectral sensitivity of the camera can be examined or calibrated with regard to the edge evaluation.

Furthermore, the calibration structure 1 can alternatively or additionally also consist of a glass carrier, on which a so-called polarization filter is realized by a coating. For this purpose, in general, thin metal layers having a fine strip structure are deposited on the glass carrier. The wire grid polarizers thus produced allow only the electromagnetic waves that are linearly polarized transversely with respect to the strip structure to pass through the polarizer. Particularly in conjunction with an LED or LCD light source as transmitted-light illumination unit 26 of the optical measuring device 10, i.e., with a light source that by itself generally generates linearly polarized illumination light, it is possible to generate the effect of the calibration structure 1 according to an exemplary embodiment of the invention during use of the transmitted-light illumination unit 26 by virtue of the fact that in this case the zones 2 with the corresponding coating block the polarized illumination light during passage through the calibration structure 1.

Furthermore, the respectively mutually different optical properties of the zones 2 of the calibration structure 1 according to the exemplary embodiment of the invention shown in FIG. 4 can be given only for a specific wavelength in the range of between 400 nm and 700 nm and the respectively mutually different optical properties can have other optical properties at a different wavelength of the range, such that the ratio of the optical properties at the different wavelength is reversed in comparison with the ratio of the optical properties at the specific wavelength.

For this purpose, the calibration structure 1 can have for example zones 2 in one specific color and adjoining zones 2 in a different color, such that the calibration structure 1 during reflected-light illumination with a wavelength of, for example, 400 nm in the mutually adjoining zones has a ratio of the reflectivity which is precisely reversed in the case of the use of reflected-light illumination with a wavelength of 700 nm.

FIG. 5 shows an ideal line pattern of the calibration structure 1 according to an exemplary embodiment of the invention as a schematic illustration of the separating lines and intersection points of the calibration structure 1 according to the exemplary embodiment of the invention in accordance with FIG. 4. FIG. 5 highlights the surroundings P5 of a point of the calibration structure 1 according to the exemplary embodiment of the invention at which a plurality of zones meet, i.e., are adjoining one another, and which is distinguished as an intersection point of the straight lines 3 and the curved lines 4. In this case, the calibration structure 1 according to the exemplary embodiment of the invention has at least one region which is distinguished by a regular sequence of the zones 2 and lines 3 and 4, thus resulting in a regular arrangement of such points, such as the central point of the surroundings P5, which regular arrangement is given by a regular shortest distance with the length L of the points with respect to one another. In this case, the straight lines 3 and the curved lines 4 in the form of circle arcs begin at a point and end at a neighboring point relative thereto, wherein the length of all lines 3 and 4 beginning or ending at one of the points is greater than 4*L, in particular greater than 9*L.

In this case, the shortest distance with the length L of the intersection points of the calibration structure 1 according to the exemplary embodiment of the invention shown in FIG. 4 corresponds to the edge lengths L of a checkerboard field of the calibration structure 1a from the related art in accordance with FIG. 2 or 3. Consequently, in conjunction with the explanations with regard to FIG. 3, it is evident that the calibration structure 1 according to an exemplary embodiment of the invention significantly increases the total length of the evaluatable edges in relation to the related art, which entails an increase in the calibration accuracy or an increase in the calibration values per unit area of the measurement field. The calibration structure 1 according to the exemplary embodiment of the invention thus makes it possible to increase the evaluatable edges per unit area by almost a factor of 5 relative to comparable calibration structures 1a from the prior art with comparable edge lengths L, without, in return, the edge length L of the underlying elementary cell of the calibration structure itself having to shrink by the aforementioned factor for this purpose. Therefore, the novel calibration structure 1 according to the exemplary embodiment of the invention in accordance with FIG. 4 also evades otherwise necessary work or calibration at the resolution limit of the imaging optical unit 22 of an optical measuring device 10 by conventional calibration structures.

Because of the target-star-like surface structure of the calibration structure 1 according to the exemplary embodiment of the invention, based on known contrast evaluations, it is furthermore possible to also ascertain which points of a transition of zones 2 of the calibration structure 1 are still imaged with a sufficient resolution capability by the optical measuring device 10, and which are not. Consequently, those points for which the resolution capability is insufficient can be excluded from a further edge evaluation for the distortion calibration of the optical measuring device. Therefore, the distortion calibration is influenced only by those points of the imaged calibration structure 1 which also exhibit a sufficient contrast and thus are also beset by a low software inadequacy with regard to the edge evaluation of a zone transition. This holds true especially if, for the edge length L of the calibration structure 1 according to the exemplary embodiment of the invention, a length is chosen which is so small that it has the effect that the lines meeting at an intersection point can no longer be correctly imaged owing to lack of resolution capability of the imaging optical unit 22 of the optical measuring device.

The total length of all the edges within the surroundings P5 in FIG. 5 in the case of the calibration structure according to the exemplary embodiment of the invention is 2*L (horizontal+vertical)+√2*2*L (diagonal)+π*√2*L (8 circle segments=1 full circle) and thus is as a result rounded 9.3*L. It should be taken into consideration here that the circle segments used are just as accessible as straight lines with regard to edge evaluation on account of standard software from standard libraries. The calibration structure 1 according to the exemplary embodiment of the invention in FIG. 4 is furthermore also distinguished by the fact that it deviates particularly in the marginal region from the regular arrangement of the line and zone structure of the central region of the calibration structure 1. In this case, at least one region or one zone 2 of the calibration structure 1 is structured differently in comparison with all other regions or zones 2 of the calibration structure 1 and accordingly has a different line pattern for zone delimitation. The region or the zone 2 can be used to separate intrinsic defects of the calibration structure 1 resulting, for example, from inadequate manufacture of the calibration structure 1 from the imaging aberrations of the optical measuring device 10 by virtue of the region in question or the zone 2 in question being positioned at different field points of the measurement field by displacement of the calibration structure 1 and a calibration then being carried out in this position. It is thus possible to identify error portions in the calibration values which move concurrently with the calibration structure 1 in contrast to error portions which are present independently of this movement. However, this procedure plays a part only if it is necessary to increase the calibration accuracy of the optical measuring device 10 beyond the manufacturing accuracy of the calibration structure 1.

Figure 6:
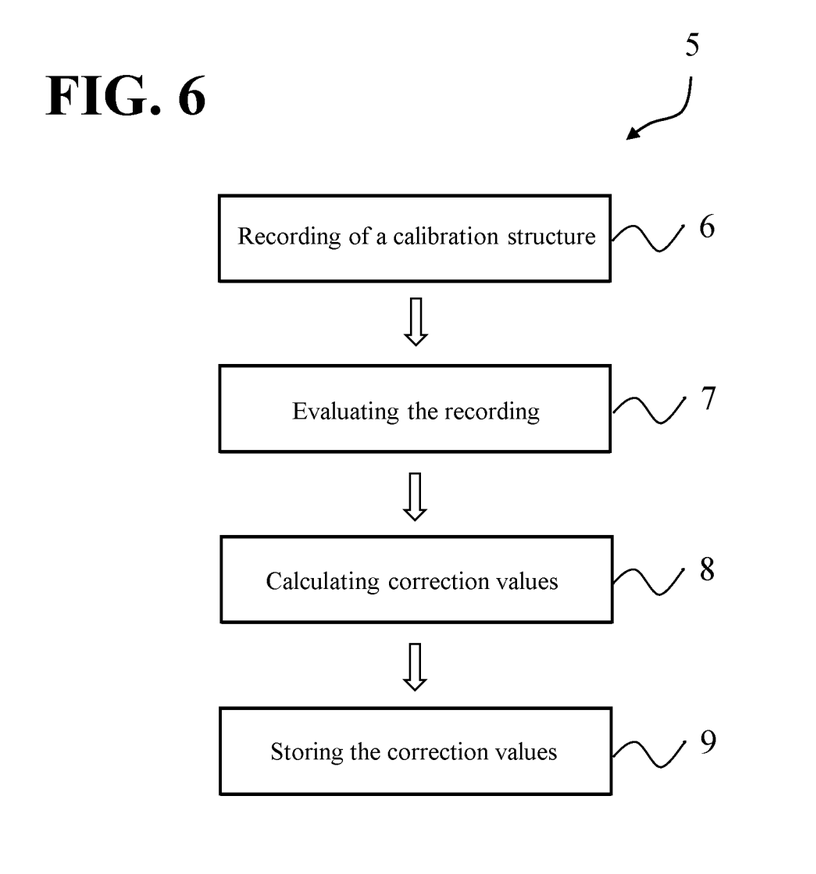
FIG. 6 shows a schematic illustration of a calibration method according to an exemplary embodiment of the invention.

FIG. 6 shows a schematic illustration of a calibration method 5 according to an exemplary embodiment of the invention for calibrating optical measuring devices 10 by a calibration structure 1 according to an exemplary embodiment of the invention. In a first preparation step, firstly the calibration structure 1 according to the exemplary embodiment of the invention is positioned within the measurement range of the optical measuring device 10. Afterward, in a second preparation step of the calibration method, the calibration structure 1 is illuminated by reflected-light and/or transmitted-light illumination. In a step 6 of the calibration method, a recording of the calibration structure 1 is then made by a sensor chip 20 of the optical measuring device 10. Afterward, in step 7, this recording made is evaluated with regard to the edge positions of the calibration structure 1 within the recording made, by a control and evaluation unit 30. Standard algorithms for edge evaluation from known libraries are used for this purpose. Based on the edge position ascertained within the recording made, in step 8, correction values are calculated under the assumption of an ideal calibration structure 1 with an ideal line pattern in accordance with FIG. 5. These correction values or calibration values are stored in a correction or calibration file or stored in a memory 32 of the optical measuring device 10 in a step 9.

In one advantageous configuration of the calibration method 5 for calibrating optical measuring devices 10, the following steps: illuminating a calibration structure 1; making a recording 6; evaluating the recording made 7 and calculating correction values 8 are carried out for two different illumination situations and/or two different illumination wavelengths and calculating correction values 8 is carried out on the basis of a consideration of the difference between the two recordings of the calibration structure 1 that are made here.

According to an exemplary embodiment of the invention, in this case, by switching over between two different illumination situations and/or two different illumination wavelengths, the ratios of the optical properties of the mutually adjoining zones of the calibration structure 1 are altered or in the optimum case reversed, such that for example a zone which is bright in the imaging of the calibration structure 1 is transformed into a dark zone, and vice versa. It is thereby possible for example to transform a bright-dark transition of an edge into a dark-bright transition of the second recording without a change in the position of the calibration structure. The software evaluation of both transitions of one and the same edge in the two recordings then makes it possible to eliminate calibration errors which are based purely on a transition being detected inadequately in terms of software, since for example the software, in the case of a transition, shifts the edge systematically too far into the bright region, or vice versa.

The described switchover from bright to dark can be achieved the most simply by the calibration structure 1 if one of the two illumination situations is given by reflected-light illumination and the other of the two illumination situations is given by transmitted-light illumination. It goes without saying, however, that the switchover according to the exemplary embodiment of the invention of the calibration method 5 is not restricted to this explained switchover from bright to dark, but also includes other optical properties of the calibration structure 1. By way of example, a specific degree of polarization of the illumination light can be set for one of the two illumination situations, which degree of polarization differs from the degree of polarization of the illumination light for the other of the two illumination situations. Likewise, one of the two different illumination wavelengths for recording the calibration structure can be less than 500 nm, wherein the other of the two different illumination wavelengths for recording the calibration structure is then more than 600 nm, for example.

It is understood that the foregoing description is that of the exemplary embodiments of the invention and that various changes and modifications may be made thereto without departing from the spirit and scope of the invention as defined in the appended claims.

What is claimed is:

1. A calibration structure for calibrating an optical edge profile measuring device, the optical edge profile measuring device comprising:
   a workpiece table;
   a camera having an imaging optical unit and being arranged at a distance from the workpiece table;
   an illumination unit configured to illuminate the calibration structure; and
   a processor configured to evaluate edge positions of the calibration structure, the calibration structure comprising:
   a plurality of zones adjoining one another in a plane and along at least one of straight lines and curved lines;
   the plurality of zones including first zones adjoining one another along the straight lines and second zones adjoining one another along the curved lines;
   the first zones adjoining one another along the straight lines or the second zones adjoining one another along the curved lines having respectively mutually different optical properties;
   points at which the zones adjoin one another and which are distinguished as intersection points of the straight lines and the curved lines; and
   at least one region with a regular sequence of the zones and the straight and curved lines which results in a regular arrangement of the points within the at least one region,
   wherein the regular arrangement is given by a regular shortest distance with the length L of the points with respect to one another,
   wherein the straight lines and the curved lines in a form of circle arcs begin at a point and end at a neighboring point relative to the point, and
   wherein a length of all lines beginning or ending at the point is greater than 4*L.

2. The calibration structure as claimed in claim 1, wherein the respectively mutually different optical properties are complementary optical properties of a zone and a respective other zone.

3. The calibration structure as claimed in claim 1, wherein the optical properties comprise at least one of transmissivity, reflectivity and polarization capability.

4. The calibration structure as claimed in claim 1, further comprising:
a plate-shaped substrate material,
wherein optical properties of a subset of the zones result from a coating of the plate-shaped substrate material.

5. The calibration structure as claimed in claim 4, wherein the plate-shaped substrate material is a plate-shaped glass carrier and the coating is a chromium coating.

6. The calibration structure as claimed in claim 4, wherein the plate-shaped substrate material is a plate-shaped glass carrier and the coating defines a bandpass filter which transmits more illumination light having a wavelength of less than 500 nm at a vertical incidence angle than illumination light having a wavelength of more than 600 nm.

7. The calibration structure as claimed in claim 4, wherein the plate-shaped substrate material is a plate-shaped glass carrier and the coating defines a bandpass filter, which transmits less illumination light having a wavelength of less than 500 nm at a vertical incidence angle than illumination light having a wavelength of more than 600 nm.

8. The calibration structure as claimed in claim 4, wherein the plate-shaped substrate material is a plate-shaped glass carrier and the coating defines a polarization filter.

9. The calibration structure as claimed in claim 1, wherein the respectively mutually different optical properties are given only for a specific wavelength in a range of between 400 nm and 700 nm and the respectively mutually different optical properties have other optical properties at a different wavelength of the range to permit a ratio of the optical properties at the different wavelength to be reversed in comparison with a ratio of the optical properties at the specific wavelength.

10. The calibration structure as claimed in claim 1, further comprising:
points at which the zones adjoin one another and which are distinguished as intersection points of the straight lines and the curved lines; and
at least one region with a regular sequence of the zones and the straight and curved lines which results in a regular arrangement of the points within the at least one region,
wherein the regular arrangement is given by a regular shortest distance with the length L of the points with respect to one another,
wherein the straight lines and the curved lines in a form of circle arcs begin at a point and end at a neighboring point relative to the point, and
wherein a length of all lines beginning or ending at the point is greater than 9*L.

11. The calibration structure as claimed in claim 1, further comprising:
at least one further region with at least one further zone, wherein the at least one further region is a region without a sequence of the zones and the straight and curved lines.

12. The calibration structure as claimed in claim 1, further comprising:
at least one further region with at least one further zone, wherein the at least one further region has a sequence of the zones and the straight and curved lines that is different from the regular sequence of the at least one region with the regular sequence of the zones and the straight and curved lines.

13. A calibration method for calibrating the optical edge profile measuring device by the calibration structure as claimed in claim 1, the method comprising:
positioning the calibration structure within a measurement range of the optical edge profile measuring device;
illuminating the calibration structure by at least one of a reflected-light illumination and a transmitted-light illumination;
recording of the calibration structure by a sensor chip of the optical edge profile measuring device;
evaluating the recording regarding the edge positions of the calibration structure within the recording;
calculating correction values based on an ascertained edge position; and
storing the correction values in a correction file.

14. The calibration method as claimed in claim 13, further comprising:
carrying out the illuminating of the calibration structure, the recording, the evaluating of the recording and the calculating of the correction values for at least one of two different illuminations and two different illumination wavelengths; and
carrying out the calculating of the correction values based on a difference between two recordings of the calibration structure with the at least one of the two different illuminations and the two different illumination wavelengths.

15. The calibration method as claimed in claim 14, wherein one of the two illuminations is the reflected-light illumination and the other one of the two illuminations is the transmitted-light illumination.

16. The calibration method as claimed in claim 15, further comprising:
setting a specific degree of polarization of illumination light for one of the two illuminations which differs from a degree of the polarization of the illumination light set for the other one of the two illuminations.

17. The calibration method as claimed in claim 14, wherein one of the two different illumination wavelengths for recording the calibration structure is less than 500 nm, and wherein the other of the two different illumination wavelengths for recording the calibration structure is greater than 600 nm.

* * * * *